United States Patent [19]

Klingler et al.

[11] Patent Number: 5,696,305
[45] Date of Patent: Dec. 9, 1997

[54] PROCESS FOR THE PRODUCTION OF NITROAROMATIC COMPOUNDS

[75] Inventors: Uwe Klingler, Dormagen; Thomas Schieb, Rösrath; Gerhard Wiechers, Leverkusen, all of Germany; Jürgen Zimmermann, Walnut Creek, Calif.

[73] Assignee: Bayer Aktiengesellschaft, Leverkusen, Germany

[21] Appl. No.: 510,888

[22] Filed: Aug. 3, 1995

[30] Foreign Application Priority Data

Aug. 11, 1994 [DE] Germany ............... 44 28 460.8

[51] Int. Cl.$^6$ ............... C07C 205/06
[52] U.S. Cl. ............... 568/934; 568/927; 568/932
[58] Field of Search ............... 568/934, 932, 568/927

[56] References Cited

U.S. PATENT DOCUMENTS

| | | | |
|---|---|---|---|
| 4,367,347 | 1/1983 | Sawicki | 568/934 |
| 4,772,757 | 9/1988 | Lailach et al. | 568/939 |
| 5,345,012 | 9/1994 | Schieb et al. | 568/934 |

FOREIGN PATENT DOCUMENTS 2309712  8/1974  Germany.

OTHER PUBLICATIONS

Bodenbrenner, von Plessen, Vollmüller, Dechema–Monogr. 86 1980, 197.
Winnacker, Küchler, Chem. Technol., vol. 2, Anorg. Technol. I, 4th Edition, 1982 pp. 70–72.
R.A. Vauck, H.A. Müller, Grundoperationen Chemischer Verfahrenstechnik, 5th Edition, VEB Leipzig 1962 p. 447.

*Primary Examiner*—Marianne M. Cintins
*Assistant Examiner*—Dwayne C. Jones
*Attorney, Agent, or Firm*—Joseph C. Gil; Lyndanne M. Whalen

[57] ABSTRACT

Nitroaromatic compounds are produced by continuously reacting an aromatic compound with nitrating acid. The reaction mixture is separated into an organic phase from which the desired nitroaromatic compound is recovered and an acid phase. The acid phase is subjected to flash evaporation to remove at least 5% by weight of the water present therein. The vapors generated during the flash evaporation are introduced into a jet spray of coolant to produce a condensate made up coolant, condensed vapors and suspended organic compounds. A portion of the condensate is subjected to phase separation to remove water and organic compounds present therein. The water and organic compounds may be reused. The process of the present invention is particularly advantageous in that deposits which block pipelines and interfere with heat transfer are not generated.

5 Claims, 1 Drawing Sheet ic acid made up of from about 80 to about 100% by
weight (based on total weight of nitrating acid) of inorganic
materials which include from about 60 to about 90% by

PROCESS FOR THE PRODUCTION OF NITROAROMATIC COMPOUNDS

BACKGROUND OF THE INVENTION

The present invention relates to a continuous process for the production of nitroaromatic compounds by nitration of aromatic compounds with nitrating acid.

Nitroaromatic compounds are intermediate products for plastics precursors, dyes, plant protection agents, pharmaceuticals and explosives. Nitroaromatic compounds are obtained by reacting an aromatic starting compound with nitric acid (Ullmanns, *Encyklopädie der technischen Chemie*, 4th Edition, Vol. 17, page 383). Sulfuric acid is used as an auxiliary in such processes. Water is formed as a secondary product in the nitration reaction and dilutes the sulfuric acid. The dilute sulfuric acid thus obtained has to be concentrated so that it can be reintroduced into the process in the original concentration.

The concentration process may be carried out under normal pressure by the Pauling-Plinke process (Bodenbrenner, von Plessen, Vollmüller, *Dechema-Monogr.* 86 (1980), 197). In this process, the acid to be concentrated is introduced through a fractionating column into a heated tank reactor containing boiling concentrated sulfuric acid.

In another known process, the sulfuric acid is concentrated in one or more stages carried out in vacuo under reduced pressure (Winnacker, Küchler, *Chem. Technol.*, Vol. 2, *Anorg. Technol. I*, 4th Edition, (1982), pages 70 to 72).

One particular embodiment of this vacuum process is often carried out after adiabatic nitration processes. In this embodiment, the hot sulfuric acid to be concentrated coming from the reactor is directly exposed to the vacuum and the water is driven off overhead. The concentrated acid collects at the bottom.

One feature common to each of these concentration processes is the distillation of organic compounds dissolved in the sulfuric acid over with the water. The organic compounds are then condensed with the water. The organic compounds which solidify at temperatures above the condensation point of the steam change into the solid aggregate state and consequently cover and inactivate the heat transfer surfaces of the condensers. This occurs, for example, in the concentration of waste acids from the production of dinitrotoluene. In this case, cooling water (preferably at a temperature of 20° C. or lower) is used to condense water under the prevailing pressure conditions. However, the dinitrotoluene isomer mixture solidifies at a temperature of only about 55° C.

It is known from the literature that coating of the heat transfer surfaces with condensed organic compounds can be avoided by using timed cyclic heat exchangers. Cyclic heat exchangers are used in alternation, being cleaned (for example, by melting) during the inoperative phase. However, the heat transfer surfaces still become coated during the process so that the passage of heat is impeded. Another disadvantage of cyclic heat exchangers is the frequency with which the heat exchangers have to be alternated.

In another known process, a suitable solvent is sprayed into the vapors in order to dissolve the organic compounds in the solvent and keep them liquid. The disadvantage of this process is that a suitable solvent is often not available or cannot be tolerated in the process for safety reasons or quality reasons. Thus, in the process disclosed in DE-A 2,309,719, for example, mononitrotoluene is introduced into the vapor stream in the concentration of spent sulfuric acid from the production of dinitrotoluene in order to prevent the dinitrotoluene from crystallizing out. However, this is only possible because, in this case, dinitrotoluene is produced by a two-stage process involving mononitrotoluene as an intermediate product so that the mononitrotoluene used is available in situ. If dinitrotoluene is produced in a single stage, as described in EP-A 0,066,202, for example, no mononitrotoluene is obtained as an intermediate product so that the mononitrotoluene sprayed into the vapor stream has to be brought in.

Directly contacting the vapor to be condensed with the cooling medium, i.e. precipitating the vapors, for example, by spraying in cold liquids, is a well known industrial process (mixing or injection condenser, cf. R. A. Vauck, H. A. Müller, *Grundoperationen chemischer Verfahrenstechnik*, 5th Edition, VEB Leipzig 1962, page 447). This technique is problematical where organic compounds which solidify at a point just above the condensation temperatures are present. Due to the high solidification rate, amorphous tacky deposits are formed and lead to the blockage of pipelines and fittings and to the formation of wall coatings in heat exchangers.

SUMMARY OF THE INVENTION

It is an object of the present invention to provide a process for producing nitroaromatic compounds in which the vapors generated during the concentration of sulfuric acid from the nitration process are effectively condensed.

It is also an object of the present invention to provide a process for producing nitroaromatic compounds in which the formation of a coating on the heat transfer surfaces is avoided.

It is another object of the present invention to provide a process for the production of nitroaromatic compounds in which solvent need not be used to dissolve any deposits formed.

These and other objects which will be apparent to those skilled in the art are accomplished by continuously reacting an aromatic compound with a nitrating acid, separating the reaction mixture into an organic phase and an acid phase and recovering the desired nitroaromatic product from the organic phase. The acid phase is subjected to flash evaporation to remove at least 5% by weight of the water present therein. The vapors generated during such flash evaporation are introduced into a jet spray of coolant to condense those vapors and form a condensate which includes coolant, condensed vapors and suspended organic compounds. A portion of this condensate is subjected to phase separation to remove water and organic compounds. The removed water and organic compounds may then be reused.

BRIEF DESCRIPTION OF THE DRAWING

The FIGURE illustrates schematically the apparatus used to carry out the process of the present invention described in the Example.

DETAILED DESCRIPTION OF THE PRESENT INVENTION

Figure 1:
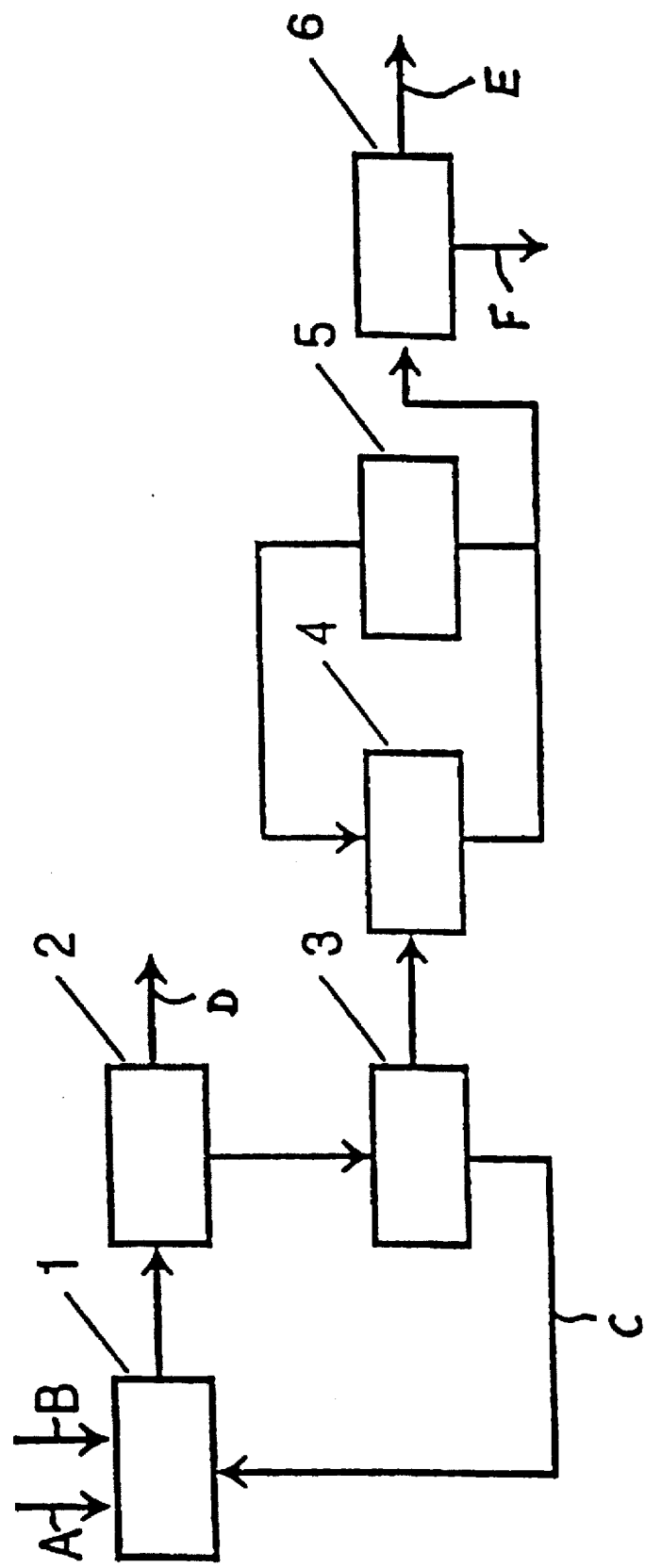

The present invention relates to a process for the continuous production of nitroaromatic compounds. In this process, an aromatic compound is reacted in a reactor using a nitrating acid made up of from about 80 to about 100% by weight (based on total weight of nitrating acid) of inorganic materials which include from about 60 to about 90% by weight (based on the total weight of inorganic materials) sulfuric acid, from about 1 to about 20% by weight (based on the total weight of inorganic materials) nitric acid and at least 5% by weight (based on the total weight of inorganic materials) water and from 0 to about 20% by weight of organic materials (based on total nitrating acid) which include from about 70 to about 100% by weight (based on the total weight of organic materials) of nitrated aromatic compounds and from 0 to about 30% by weight (based on the total weight of organic materials) by-products of the nitration reaction. The aromatic compound and nitrating acid are used in amounts such that the molar ratio of nitric acid to aromatic compound is from about 0.8:1 to about 2.5:1 (established as a function of the nitration process). The reaction mixture leaves the reactor in which the nitration reaction was conducted at a temperature of at least 80° C. and is separated into a upper product phase and a lower acid phase. The product phase is worked up to recover the desired nitroaromatic product. The acid phase containing organic compounds is freed from at least 5% by weight of the water by flash evaporation, optionally with simultaneous application of heat. After the flash evaporation, the vapors generated during such evaporation are introduced directly into the jet spray of a coolant, preferably water, in vacuo, so that the vapors are condensed. The condensate is made up of coolant, condensed vapors and suspended organic compounds. A portion of this condensate is circulated and cooled. The remainder of the condensate is subjected to phase separation. The water removed is conditioned and the organic compounds removed are reused.

In a preferred embodiment, the condensate composed of coolant, condensed vapors and suspended organic compounds which is to be subjected to phase separation is heated to such an extent that the organic compounds are present in liquid form before being subjected to phase separation. This makes it possible to use liquid/liquid phase separation.

However, the organic compounds may also be removed from the remaining condensate in solid form.

Toluene, benzene, chlorobenzene and xylene are preferably used as the aromatic compounds to be nitrated in accordance with the present invention.

In the process of the present invention, the aromatic compounds are mononitrated or dinitrated.

Despite the extremely unfavorable solidification and crystallization conditions, the organic compounds do not form any sticky deposits during condensation of the vapors in the process of the present invention. Instead, they form fine hard crystals which give a stable suspension which does not lead to blockages or coatings.

Having thus described our invention, the following Example is given as being illustrative thereof. All percentages given in this Example are percentages by weight. The equipment used to carry out the process of the present invention in this Example is illustrated schematically in the FIGURE.

EXAMPLE

In three-stage jet tube reactor 1, 5.1 kg/h (55.0 moles/h) of toluene (shown in the FIGURE as stream A) and 12.4 kg/h (118.1 moles/h) of 60% nitric acid (shown in the FIGURE as stream B) were reacted with 209 kg/h of waste acid (shown in the FIGURE as stream C) from the acid concentration stage 3. The reaction mixture leaving the reactor 1 at a temperature of 160° C. was subjected to phase separation in separator 2. 9.6 kg/h of dinitrotoluene (shown in the FIGURE as stream D) were obtained as product. The acidic phase (216 kg/h of 80% by weight sulfuric acid) was concentrated to 82.8% by weight in acid concentrator 3 under a pressure of 50 mbar. The concentrated waste acid (stream C) was returned to the reactor at a temperature of 130° C.

In condenser 4 which had a volume of 100 l, the hot (130° C.) vapors composed of 6.6 kg/h of steam and 0.4 kg/h of dinitrotoluene were continuously condensed in the jet spray of a solid cone nozzle under a system pressure of 50 mbar. The cooling water entry temperature was 25° C. The dinitrotoluene accumulated in the form of a crystalline solid suspended in water. An increase in temperature of 5° C. occurred. The cooling water/condensate mixture removed from condenser 4 was partly cooled in heat exchanger 5 and returned as cooling medium to condenser 4. A volumetric flow rate of 1 m³/h was established in the circuit. The remaining mixture was heated to 60° C. in a heat exchanger at a rate of 6.89 kg/h. The organic phase F was then separated from the aqueous phase E in gravity separator 6 (liquid/liquid phase separation). There were no blockages in the nozzle and no deposits in the pipes and fittings. Nor were any coatings formed on the heat transfer surfaces.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the continuous production of nitroaromatic compounds comprising A) reacting an aromatic compound with a nitrating acid composed of
  1) from about 80 to about 100% by weight inorganic materials which include
    a) from about 60 to about 90% by weight sulfuric acid,
    b) from about 1 to about 20% by weight nitric acid, and
    c) at least 5% by weight water and
  2) from 0 to about 20% by weight of organic materials which include
    a) from about 70 to 100% by weight nitrated aromatic compounds and
    b) from 0 to about 30% by weight by-products of the nitration reaction in a reactor in amounts such that the molar ratio of nitric acid to aromatic compound is from about 0.8:1 to about 2.5:1, B) removing the reaction mixture from the reactor at a temperature of at least 80°, C) separating the mixture from B) into an upper organic product phase and a lower acid phase, D) recovering the nitroaromatic compound from the organic product phase separated in C), E) treating the acid phase separated in C) by flash evaporation to remove at least 5% by weight water, F) introducing the vapors generated in E) into a jet spray of coolant in vacuo to condense the vapors to form a condensate which includes coolant, condensed vapors and suspended organic compounds, G) circulating and cooling a first portion of the condensate formed in F), H) subjecting a second portion of the condensate formed in F) to phase separation to remove water and organic compounds present therein, and I) musing the water and organic compounds removed in H).

2. The process of claim 1 in which heat is applied during the flash evaporation of step E).

3. The process of claim 1 in which the second portion of condensate formed in F) is heated to such an extent that the organic compounds are present in liquid form prior to phase separation in step H).

4. The process of claim 1 in which the aromatic compound to be nitrated is selected from toluene, benzene, chlorobenzene and xylene.

5. The process of claim 1 in which the aromatic compound to be nitrated is toluene.

* * * * *